United States Patent [19]
McKay

[11] Patent Number: 6,037,519
[45] Date of Patent: Mar. 14, 2000

[54] CERAMIC FUSION IMPLANTS AND COMPOSITIONS

[75] Inventor: William F. McKay, Memphis, Tenn.

[73] Assignee: SDGI Holdings, Inc., Memphis, Tenn.

[21] Appl. No.: 08/955,003

[22] Filed: Oct. 20, 1997

[51] Int. Cl.$^7$ .................................. A61F 2/28; A61F 2/44
[52] U.S. Cl. .............................. 623/16; 623/17; 423/305; 423/311; 424/423; 523/115; 524/415
[58] Field of Search .................................. 623/11, 16, 17; 606/60, 61; 423/305, 307, 308, 311; 427/2.24, 2.26, 2.27; 523/113–116; 524/415; 424/422, 423, 424, 425

[56] References Cited

U.S. PATENT DOCUMENTS

| | | | |
|---|---|---|---|
| 4,097,935 | 7/1978 | Jarcho | 3/1.9 |
| 4,294,753 | 10/1981 | Urist . | |
| 4,596,574 | 6/1986 | Urist | 623/16 |
| 4,820,305 | 4/1989 | Harms et al. . | |
| 4,877,864 | 10/1989 | Wang et al. . | |
| 4,878,915 | 11/1989 | Brantigan . | |
| 4,961,740 | 10/1990 | Ray et al. . | |
| 5,013,649 | 5/1991 | Wang et al. . | |
| 5,015,247 | 5/1991 | Michelson . | |
| 5,026,373 | 6/1991 | Ray et al. . | |
| 5,106,748 | 4/1992 | Wozney et al. . | |
| 5,108,922 | 4/1992 | Wang et al. . | |
| 5,116,738 | 5/1992 | Wang et al. . | |
| 5,147,402 | 9/1992 | Bohler et al. . | |
| 5,187,076 | 2/1993 | Wozney et al. . | |
| 5,192,327 | 3/1993 | Brantigan . | |
| 5,306,303 | 4/1994 | Lynch | 623/16 |
| 5,366,875 | 11/1994 | Wozney et al. | 435/69.1 |
| 5,464,440 | 11/1995 | Johansson | 623/16 |
| 5,702,449 | 12/1997 | McKay | 623/17 |
| 5,756,457 | 5/1998 | Wang et al. | 514/12 |
| 5,769,897 | 6/1998 | Harle | 623/17 |

FOREIGN PATENT DOCUMENTS

| | | |
|---|---|---|
| 0 616 814 A1 | 9/1994 | European Pat. Off. . |
| WO 93/00432 | 1/1993 | WIPO . |
| WO 94/26892 | 11/1994 | WIPO . |
| WO 94/26893 | 11/1994 | WIPO . |
| WO 96/40014 | 12/1996 | WIPO .............................. A61F 2/44 |

OTHER PUBLICATIONS

Jeffrey M. Toth et al.: "Evaluation of Porous Biphasic Calcium Phosphate Ceramics for Anterior Cervical Interbody Fusion in a Caprine Model"—*Spine* vol. 20, No. 20, pp. 2203–2210, XP–002055736.

*Primary Examiner*—Mickey Yu
*Assistant Examiner*—Tram A. Nguyen
*Attorney, Agent, or Firm*—Woodard, Emhardt, Naughton, Moriarty & McNett

[57] ABSTRACT

Bone graft substitute compositions are provided for promoting new bone growth and arthrodesis. The compositions include a carrier for controlled delivery of osteoinductive factors. In one embodiment, the carriers include a biphasic calcium phosphate ceramic having between about 2–40% hydroxyapatite and about 98–60% tricalcium phosphate by volume, and a calcium/phosphorous ratio of between about 1.50 to about 1.60. The invention also includes osteoinductive compositions including the carriers and an effective amount of a bone morphogenetic protein dispersed within the ceramic. The composition has a weight ratio of protein to ceramic of no more than about 1:200. In a specific embodiment, the weight ratio of protein to ceramic is between about 1:200 and about 1:2000. Spinal implants (10) are also provided which include a body (11) having a wall (12) sized for engagement within a space (S) between adjacent vertebrae (V) to maintain the space (S) and a confining matrix (13) for confining new bone growth to the body (11). The matrix (13) includes a biphasic calcium phosphate ceramic which degrades at a rate to provide calcium and phosphate for the new bone growth without reduced density of bone adjacent the space and an effective amount of a substantially pure osteogenic factor bound to the ceramic.

50 Claims, 4 Drawing Sheets

CERAMIC FUSION IMPLANTS AND COMPOSITIONS

FIELD OF THE INVENTION

The present invention relates to bone graft substitute compositions and implants for new bone formation and arthrodesis. In specific applications of the invention the compositions include biocompatible calcium phosphate ceramics in synergistic combination with osteogenic compositions.

BACKGROUND OF THE INVENTION

Many techniques have been developed for correcting bone defects and voids In one approach, the void is filled with a bone paste or bone compound. In other techniques, the void is filled with a coralline substance. In these approaches, one goal is to induce the formation of new bone from the patient's existing bone to fill the void or repair the defect.

Aspects of these techniques have also been borrowed for application in other orthopedic procedures, such as spinal fusion. Spinal fusion is indicated to provide stabilization of the spinal column for painful spinal motion and disorders such as structural deformity, traumatic instability, degenerative instability, and post-resection iatrogenic instability. Fusion, or arthrodesis, is achieved by the formation of an osseous bridge between adjacent motion segments. This can be accomplished within the disc space, anteriorly between contiguous vertebral bodies or posteriorly between consecutive transverse processes, laminae or other posterior aspects of the vertebrae.

An osseous bridge, or fusion mass, is biologically produced by the body upon skeletal injury. This normal bone healing response is used by surgeons to induce fusion across abnormal spinal segments by recreating spinal injury conditions along the fusion site and then allowing the bone to heal. A successful fusion requires the presence of osteogenic or osteopotential cells, adequate blood supply, sufficient inflammatory response, and appropriate preparation of local bone. This biological environment is typically provided in a surgical setting by decortication, or removal of the outer, cortical bone to expose the vascular, cancellous bone, and the deposition of an adequate quantity of high quality graft material.

A fusion or arthrodesis procedure is often performed to treat an anomaly involving an intervertebral disc. Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosis. In a healthy, undamaged spine, the annulus fibrosis prevents the nucleus pulposus from protruding outside the disc space.

Spinal discs may be displaced or damaged due to trauma, disease or aging. Disruption of the annulus fibrosis allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts are often used to fill the intervertebral space to prevent disc space collapse and promote fusion of the adjacent vertebrae across the disc space. In early techniques, bone material was simply disposed between the adjacent vertebrae, typically at the posterior aspect of the vertebrae, and the spinal column was stabilized by way of a plate or rod spanning the affected vertebrae. Once fusion occurred, the hardware used to maintain the stability of the segment became superfluous and was a permanent foreign body. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intra-discal implant that could be used to replace a damaged disc and maintain the stability of the disc interspace between the adjacent vertebrae, at least until complete arthrodesis is achieved. To be successful, the implant must provide temporary support and allow bone ingrowth. Success of the discectomy and fusion procedure requires the development of a contiguous growth of bone to create a solid mass because the implant may riot withstand the cyclic compressive spinal loads for the life of the patient.

Many attempts to restore the intervertebral disc space after removal of the disc have relied on metal devices. U.S. Pat. No. 4,878,915 to Brantigan teaches a solid metal plug. U.S. Pat. Nos. 5,044,104; 5,026,373 and 4,961,740 to Ray; U.S. Pat. No. 5,015,247 to Michelson and U.S. Pat. No. 4,820,305 to Harms et al., U.S. Pat. No. 5,147,402 to Bohler et al. and U.S. Pat. No. 5,192,327 to Brantigan teach hollow metal cage structures. Unfortunately, due to the stiffness of the material, some metal implants may stress shield the bone graft, increasing the time required for fusion to occur. Subsidence, or sinking of the device into bone, is also a concern when metal implants are implanted between vertebrae. Metal devices are also foreign bodies which can never be fully incorporated into the fusion mass. Moreover, fusion rates can be slower with metal implants as compared to graft.

Various bone grafts and bone graft substitutes have also been used to promote osteogenesis and to avoid the disadvantages of metal implants. Autograft is often preferred because it is osteoinductive. Both allograft and autograft are biological materials which are replaced over time with the patient's own bone, via the process of creeping substitution. Over time a bone graft virtually disappears unlike a metal implant which persists long after its useful life. Unfortunately, the use of autograft presents several disadvantages. Autograft is available in only limited quantities. The additional surgery also increases the risk of infection and blood loss and may reduce structural integrity at the donor site. Furthermore, some patients complain that the graft harvesting surgery causes more short-term and long-term pain than the fusion surgery.

Allograft material, which is obtained from donors of the same species, is more readily obtained. However, allograft is also disadvantageous because of the risk of disease transmission and immune reactions as well as religious objections. Furthermore, allogenic bone has limited osteoinductive potential compared to autogenous bone and therefore may provide only temporary support. The slow rate of fusion using allografted bone can lead to collapse of the disc space before fusion is accomplished.

Both allograft and autograft present additional difficulties. Graft alone may not provide the stability required to withstand spinal loads. Internal fixation can address this problem but presents its own disadvantages such as the need for more complex surgery as well as the disadvantages of metal fixation devices. Also, the surgeon is often required to repeatedly trim the graft material to obtain the correct size to fill and stabilize the disc space. This trial and error approach increases the length of time required for surgery. Furthermore, the graft material usually has a smooth surface which may not provide a good friction fit between the adjacent vertebrae. Slippage of the graft may cause neural and vascular injury, as well as collapse of the disc space. Even where slippage does not occur, micromotion at the graft/fusion-site interface may disrupt the healing process that is required for fusion.

Due to the need for safer bone graft materials, bone graft substitutes, such as bioceramics, have recently received considerable attention. The challenge has been to develop a bone graft substitute which avoids the disadvantages of metal implants and bone grafts while capturing the advantages of both. Calcium phosphate ceramics are biocompatible and do not present the infectious or immunological concerns of allograft materials. Ceramics may be prepared in any quantity which is a great advantage over autograft bone graft material. Furthermore, bioceramics are osteoconductive, stimulating osteogenesis in bony sites. Bioceramics provide a porous matrix which further encourages new bone growth. Unfortunately, ceramic implants typically lack the strength to support high spinal loads and therefore require separate fixation before the fusion.

Of the calcium phosphate ceramics, hydroxyapatite (HA) and tricalcium phosphate (TCP) ceramics have been most commonly used for bone grafting. Hydroxyapatite is chemically similar to inorganic bone substance and biocompatible with bone. However, it is slowly degraded. β-tricalcium phosphate is rapidly degraded in vivo and is too weak to provide support under the cyclic loads of the spine until fusion occurs. Developing an implant having the biomechanical properties of metal and the biological properties of bone without the disadvantages of either has been extremely difficult or impossible.

In any application involving the formation of new bone, the orthopedic surgeon is concerned first that the new bone formation be complete, and second that the creation of the new bone occur as rapidly as possible. In the case of spinal fusion, another concern is that the spinal segments be adequately supported and stabilized until arthrodesis occurs. Orthopedics practitioners have long sought compositions and implants that provide optimum performance to address these and other critical concerns.

Thus far, a need remains for a bone graft substitute composition that provides this optimum performance and that can have wide applicability in the treatment of orthopedic conditions. In the field of spinal fusion, a need has remained for fusion devices and methods which stimulate bone ingrowth and avoid the disadvantages of metal implants yet provide sufficient strength to support the vertebral column until the adjacent vertebrae are fused.

SUMMARY OF THE INVENTION

In accordance with the invention, bone graft substitute compositions are provided for new bone formation and spinal arthrodesis. The compositions include a carrier for controlled delivery of bone growth inductive factors, such as bone morphogenetic proteins. In one aspect of the invention, the carriers include a biphasic calcium phosphate ceramic having between about 2–40% hydroxyapatite and about 98–60% tricalcium phosphate by volume and preferably a calcium/phosphorous ratio of between about 1.50 to about 1.60.

In other embodiments, the carriers preferably include a biphasic calcium phosphate ceramic having between about 5–20% hydroxyapatite and about 95–80% tricalcium phosphate by volume and most preferably about 20% hydroxyapatite and about 80% tricalcium phosphate.

The invention also contemplates osteoinductive compositions including the carriers and an effective amount of a bone growth inductive factor, such as substantially pure bone morphogenetic protein, dispersed within the ceramic. The composition preferably has a weight ratio of factor to ceramic of no more than about 1:200. In specific embodiments, the weight ratio of factor to ceramic is between about 1:200 and about 1:2000.

Spinal implants are also provided which include a body having a wall sized for engagement within a space between adjacent vertebrae to maintain the space and a confining matrix for confining new bone growth to the matrix. The matrix includes a biphasic calcium phosphate ceramic which degrades at a rate to provide calcium and phosphate for the new bone growth without reduced density of adjacent host bone and an effective amount of a substantially pure osteogenic factor bound to the ceramic.

One object of the present invention is to provide a bone graft substitute composition that provides a stable matrix for rapid growth of new bone into a space, such as a bone defect, void or fusion site. A more specific object of this invention is to provide spinal implants and compositions for arthrodesis of a motion segment which exploit all of the advantages of ceramic implants while avoiding the corresponding disadvantages. Another object of the invention is to provide a spinal implant which restores the intervertebral disc space and supports a vertebral column while promoting bone ingrowth.

One benefit of this invention is that it provides a synergistic composition of a bioceramic and an osteoinductive factor. The ceramic provides a stable scaffold for bone ingrowth and through-growth while the osteoinductive factor induces bone growth to speed the fusion rate. The increased speed of fusion allows the use of a bioceramic without the need for metal cages or internal fixation.

The ceramic also advantageously provides a source of calcium and phosphate to the fusion site. Another advantage is that the ceramic provides a matrix for confining induced bone growth to the fusion site to avoid bone growth in inappropriate locations. Other objects and further benefits of the present invention will become apparent to persons of ordinary skill in the art from the following written description and accompanying figures.

DESCRIPTION OF THE PREFERRED EMBODIMENT

Figure 1:
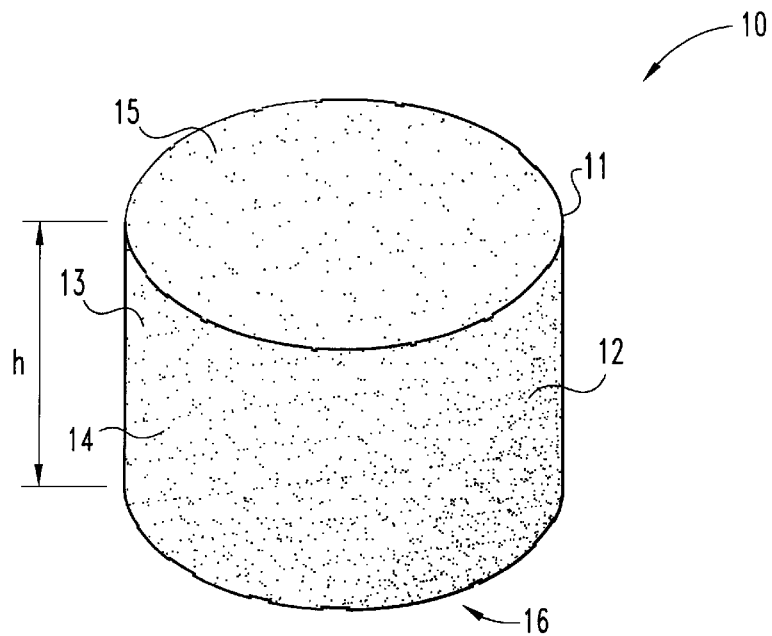
FIG. 1 is a side perspective view of a spinal implant according to this invention.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications, and applications of the principles of the invention as illustrated herein being contemplated as would normally occur to one skilled in the art to which the invention relates.

The present invention provides synergistic combinations of bioceramics with osteoinductive factors, such as bone morphogenetic proteins (BMP). The combination of the osteoinductive factor with a calcium phosphate carrier provides controlled delivery of the osteoinductive material by its natural binding to calcium phosphate and entrapped within the pores of the ceramic.

This invention provides carriers for osteoinductive factors which are optimized in terms of composition, bioactivity, porosity, pore size, protein binding potential, degradability and strength for use in both load bearing and non-load bearing grafting applications. The proper selection of bioceramic also provides slow degradation of the ceramic which results in a local source of calcium and phosphate for bone formation. Therefore, new bone can be formed without calcium and phosphate loss from the host bone surrounding the fusion site. This avoids fusion at the expense of reduced bone mineral density of adjacent host bone. The confining matrix of the ceramic prevents induced bone growth outside the carrier structure. The calcium phosphate carrier structure maintains a space for bone formation to occur and also provides a scaffold for bone ingrowth. The quicker fusion rates provided by this invention due to the osteoinductive factor compensate for the less desirable biomechanical properties of bioceramics and makes the use of internal fixation and metal interbody fusion devices unnecessary. The devices of this invention are not required to support the cyclic loads of the spine for very long because of the quick fusion rates which reduce the biomechanical demands on the implant.

In one embodiment, compositions are provided which include a carrier or matrix for controlled delivery of bone morphogenetic proteins and other bone growth inductive factors. The carriers preferably include a biphasic calcium phosphate (BCP) ceramic having hydroxyapatite and tricalcium phosphate. The ceramics can be prepared according to methods which are known in the art and can preferably include the application of a pore forming agent to form a porous ceramic. Biphasic hydroxyapatite/tricalcium phosphate (HA/TCP) is particularly preferred. In one specific embodiment, the bioceramics can be made according to materials commercially available from Sofamor Danek Group, B. P. 4-62180 Rang-du-Fliers, France and Bioland, 132 Route d:Espagne, 31100 Toulouse, France.

Both hydroxyapatite (HA) and tricalcium phosphate (TCP) have been used alone as bone graft substitutes. Hydroxyapatite acts as a scaffold for new bone formation, but undergoes little or no resorption. Moreover, HA is generally radiopaque so that it is difficult for surgeons to assess the progress of the new bone formation using x-rays. On the other hand, tricalcium phosphate has been found to resorb faster than the rate of new bone formation. Advantageously it has been discovered that biphasic ceramics provide beneficial degradation rates while the problems associated with the use of HA or TCP alone.

The carriers of this invention have between about 2–40% hydroxyapatite and about 98–60% tricalcium phosphate by volume, preferably between about 5–20% HA and about 95–80% TCP. The most preferred ratio is about 20% HA and about 80% TCP by volume. Although bone formation occurs when the carrier is comprised solely of tricalcium phosphate, the volume of bone is significantly less when compared to a hydroxyapatite/tricalcium phosphate carrier. It has been found that the presence of slower degrading hydroxyapatite in the carrier is necessary to provide better space maintenance for bone formation than a carrier composed of tricalcium phosphate alone. Although the hydroxyapatite degrades more slowly than the tricalcium phosphate, thereby providing a scaffold for continued new bone formation, too high a percentage of hydroxyapatite impedes the ability to monitor the progress of fusion. Therefore, a composite of HA/TCP will provide a good temporary scaffold, and an optimum ratio of HA to TCP will permit easier radiographic assessment of the new bone formation.

For example, carriers containing 60% hydroxyapatite and 40% tricalcium phosphate by weight have been evaluated but the resulting fusions are difficult to evaluate as this combination appears radiopaque on X-rays for long periods of time. Therefore, the optimum percentages of hydroxyapatite and tricalcium phosphate of the present invention have been carefully designed to take the above factors into account. Other advantages of having a lower percentage of hydroxyapatite in the carrier include a significantly decreased manufacturing time of the ceramic using standard precipitation methods carried out under basic pH conditions. For example, a three-fold greater reaction time is necessary to produce a biphasic ceramic comprising 60% hydroxyapatite and 40% tricalcium phosphate by weight, compared to a ceramic containing 18% hydroxyapatite and 82% tricalcium phosphate by weight.

The calcium/phosphorus ratio of the ceramics is preferably between about 1.50 to about 1.60, and most preferably 1.51. Compositions of this invention also include a pharmaceutically effective amount of a bone growth inductive factor, such as a substantially pure bone morphogenetic protein, dispersed within the ceramic. Various bone growth inductive factors are also contemplated, such as bovine extracted proteins, non-protein factors and DNA factors. Advantageously, due to the efficacy of the carrier, small quantities of the bone growth inductive factor can be used very efficiently. The composition preferably has a weight ratio of factor to ceramic of no more than about 1:200. Preferably, the weight ratio of factor to ceramic is between about 1:200 and about 1:2000. In a specific embodiment in which the factor is a recombinant human bone morphogenetic protein, the weight ratio is 1:1250.

The preferred osteoinductive factors are the recombinant human bone morphogenetic proteins (rhBMPs) because they are available in unlimited supply arid do not transmit infectious diseases. Most preferably, the bone morphogenetic protein is a rhBMP-2, rhBMP-7 or heterodimers thereof. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Pat. Nos. WO93/00432 to Wozney et al.; WO94/26893 to Celeste et al.; and WO94/26892 to Celeste t al. All osteoinductive factors are contemplated whether obtained as above or isolated from bone. Methods for isolating bone morphogenetic protein from bone are described in U.S. Pat. No. 4,294,753 to Urist and Urist et al., 81 PNAS 371, 1984.

The bone growth inductive factor may be supplied to the pores of the ceramic in any suitable manner. The osteogenic factor, preferably BMP, may be provided in freeze-dried form and reconstituted in sterile water, physiological saline, collagen gel, or any other suitable liquid or gel carrier. Any suitable medium or carrier capable of delivering the proteins to the pores of the implant is contemplated. Preferably the medium is supplemented with a buffer solution as is known in the art. The ceramic may be soaked in a solution containing the factor. Alternatively, the composition may be injected into the pores of the ceramic. In other embodiments, the composition is dripped onto the ceramic. In one specific embodiment of the invention, rhBMP-2 is suspended or admixed in a liquid carrier, such as water, saline or collagen gel. The liquid is then dripped into the pores or the ceramic is immersed in a suitable quantity of the liquid, in either case for a period of time sufficient to allow the liquid to thoroughly soak the graft.

The BCP ceramics of this invention are excellent carriers for osteoinductive factors such as bone morphogenetic proteins. Hydroxyapatite, which is very similar to the mineral phase of cortical bone, is an osteogenic factor bonding agent which controls the rate of delivery of proteins to the fusion site and contains osteoinductive factors inside the carrier. The porous structure allows mesenchymal cells to migrate into the carrier. These cells are then transformed into bone forming cells, or osteoblasts, and ultimately deposit new bone inside the carrier. The calcium phosphate compositions in this invention bind bone morphogenetic proteins and prevent BMP from prematurely dissipating from the device before fusion can occur. Retention of the BMP by the ceramic permits the protein to complete rapid bone formation and ultimately fusion across the disc space.

The BCP ratios of this invention result in more rapid and larger volume of new bone formation which allows lower dosing of osteoinductive factor. This invention exploits the discovery that HA and TCP have differential binding properties. Therefore this invention provides BCP ratios which optimize the binding potential balanced with degradability and strength. The optimized ratios result in more rapid and superior fusions. This is an improvement over prior art carriers which do not effectively bind proteins such as BMP. In some cases, TCP ceramics have released the protein too rapidly and have not provided sustained dosing of the protein. This is also disadvantageous because it allows the protein to escape the fusion site since the carrier scaffold is lost. The carriers of the present invention, however, protect the protein from being metabolized. This keeps a therapeutic level of protein at the fusion site.

This invention also provides ceramics having beneficial porosity characteristics in the case where the ceramic is formed into a block or shaped body. A porosity of between about 60% and 80%, and preferably about 70%, offers maximal porosity for bone ingrowth while still maintaining the mechanical integrity of the ceramic. The ceramics of this invention have interconnecting porosity which provide excellent wettability and surface area for protein binding as well as an optimal matrix structure for bone ingrowth. The pore size has also been optimized in this invention. The ceramics of this invention preferably have a pore size of between about 200 to about 600 microns. This pore size is optimal for bone ingrowth without compromising structural integrity.

Another significant advantage of this invention is that the BCP ceramics provide a confining matrix for confining new bone growth to the ceramic body. This can be important for applications involving areas such as the spine where vital neural and vascular tissues are exposed and vulnerable. The invasion of BMP and other osteoinductive factors into and around these tissues may cause serious complications.

In accordance with one aspect of the invention, the bone graft substitute composition is formed for introduction into a patient. In some applications, the composition is provided in the form of a porous block or body that is sized and shaped for introduction into a bone defect or void. In other applications, the composition is provided in granular form. This granular composition can be used to fill a void, disposed within the intradiscal space, or placed in the transverse interval between adjacent vertebrae, for example.

Figure 2:
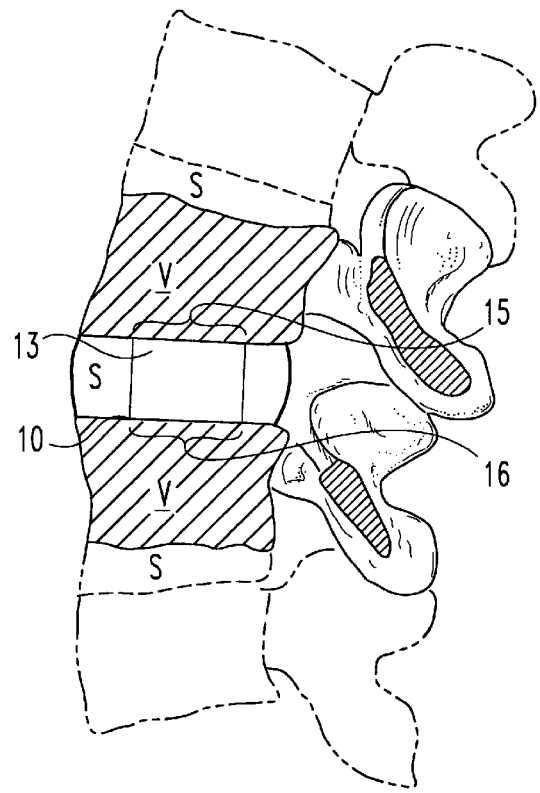
FIG. 2 is a side elevational view of a portion of a spine having the spinal implant of FIG. 1 implanted in the intervertebral space.

In one specific application, the present invention also contemplates spinal implants as depicted in FIGS. 1–5. Referring now to FIG. 1, a spinal implant 10 is provided which includes a body 11 having a wall 12 sized for engagement within a space S between adjacent vertebrae V to maintain the space S. The implant includes a confining matrix 13 for confining new bone growth to the implant 10. The confining matrix 13 includes pores 14 for containing the osteoinductive factor. The wall 12 has a height h which corresponds to the height H of the space S. In one embodiment, the height h of the wall 12 is slightly larger than the height H of the intervertebral space S. The wall 12 is adjacent to and between a superior engaging surface 15 and an inferior engaging surface 16 which are configured for engaging the adjacent vertebrae V as shown in FIG. 2.

Figure 3:
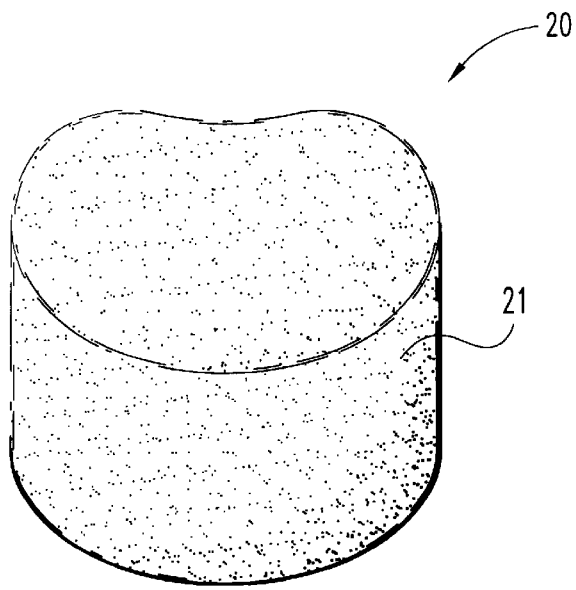
FIG. 3 depicts a kidney-shaped spinal implant according to another embodiment of this invention.
Figure 4:
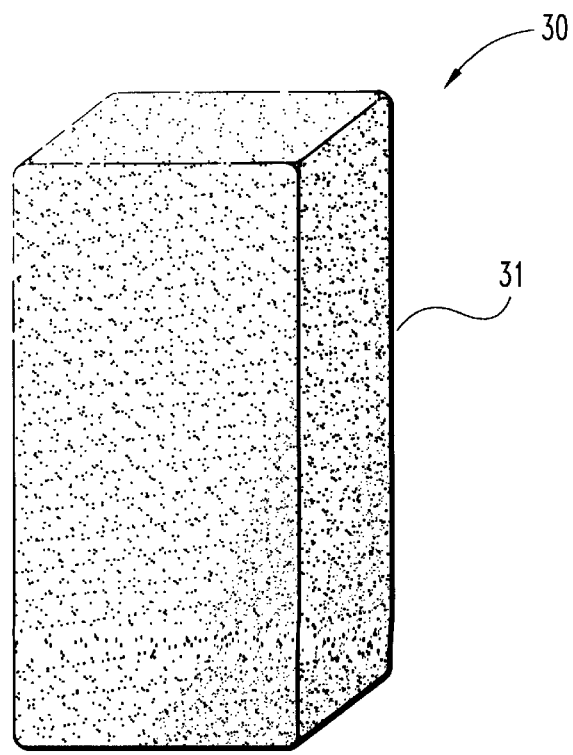
FIG. 4 is a side elevational view of another spinal implant according to this invention.

The bodies contemplated by this invention may be any suitably sized and shaped body composed of a bioceramic, preferably a BCP ceramic. Ceramics can be conveniently formed into virtually any shape. For example, the body 21 of the spinal implant 20 may be kidney-shaped as shown in FIG. 3. The shape is advantageous because it approximates the shape of a vertebral endplate. Alternatively, a spinal implant 30 may be provided which comprises a generally rectangular body 31 as shown in FIG. 4. One advantage of the embodiments of this invention is that they allow bilateral placement of spinal implants as shown in FIG. 5.

Figure 5:
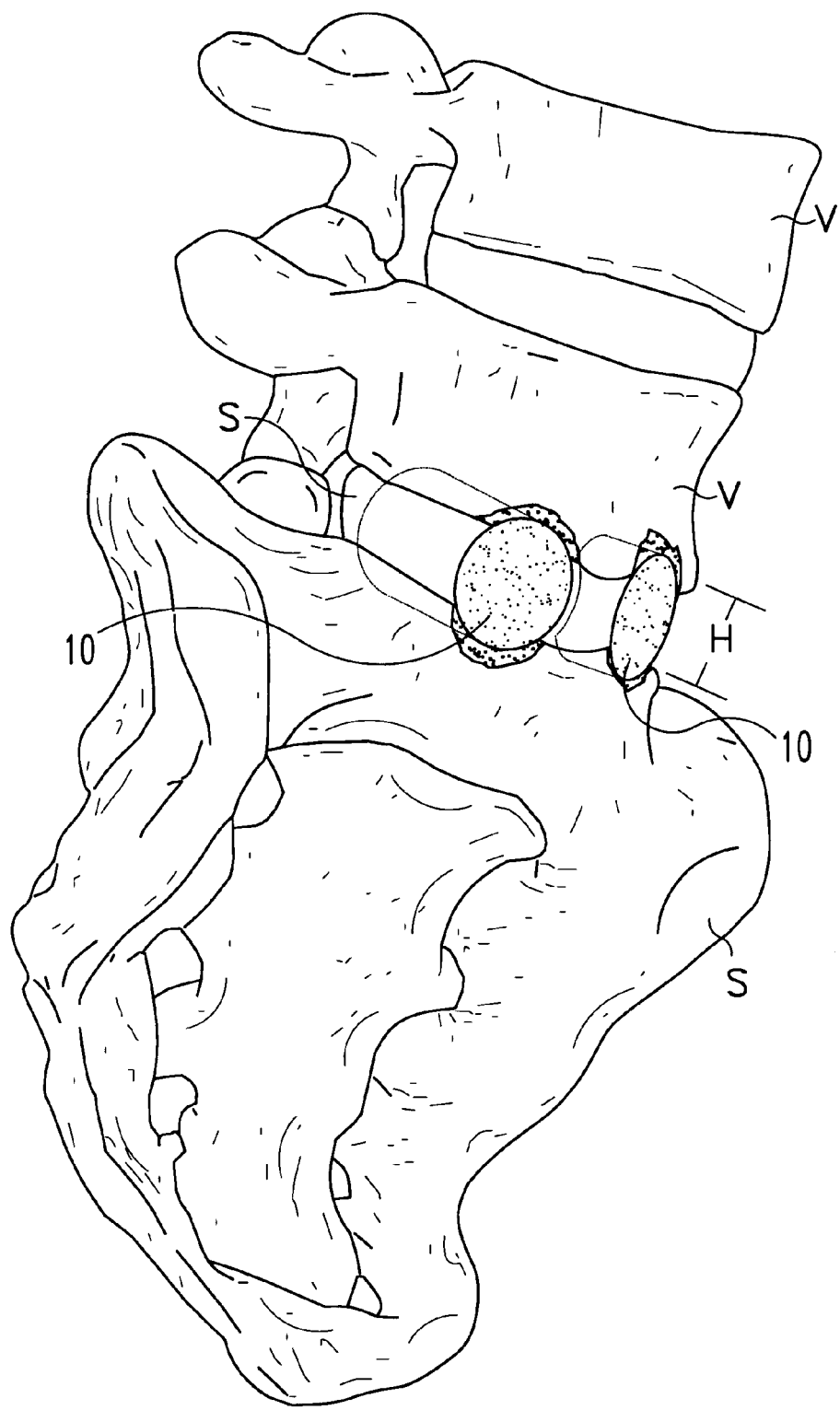
FIG. 5 is a side perspective view of a portion of the spine showing two spinal implants as shown in FIG. 1 and implanted in the intervertebral space.
Figure 6:
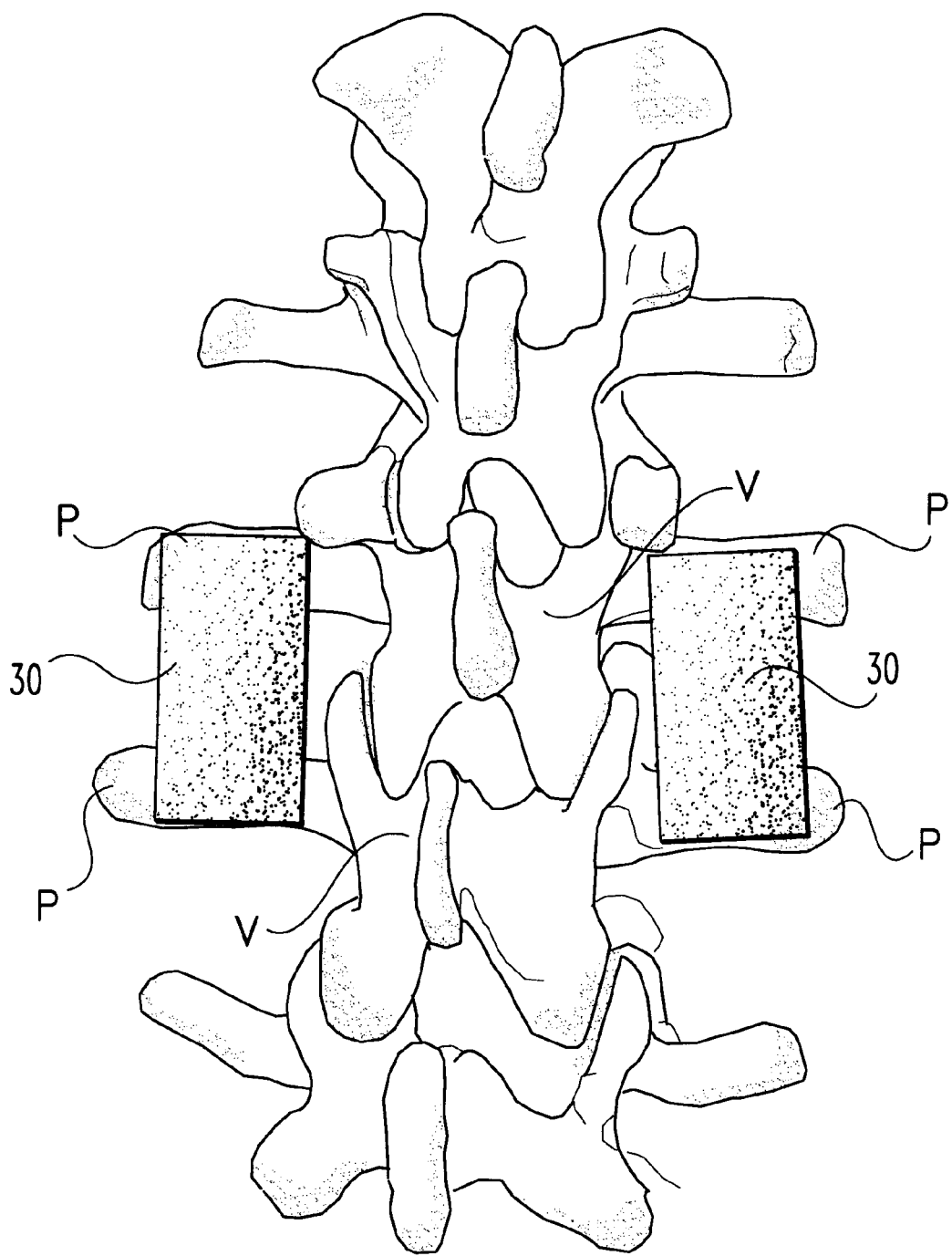
FIG. 6 is a side elevational view of a section of the spine showing spinal implants implanted bilaterally.

This invention contemplates spinal implants which can be implanted within a disc space as shown in FIGS. 2 and 5 and also spinal implants for posterolateral fusions as shown in FIG. 6. The spinal implant 30 shown in FIG. 4 is particularly suited for this application. Referring to FIG. 6, the spinal implant 30 spans and contacts the transverse processes P of adjacent vertebrae V. The implant 30 maintains a space or pocket P above and across the transverse processes for new bone formation.

The composition of the ceramic will depend on the application. Spinal implants require increased strength to support the cyclic loads of the spine until fusion occurs. The strength of these implants can be increased by increasing the hydroxyapatite content of the ceramic or by supplementing the implant with metal devices such as cages. For posterolateral fusion applications which do not have the same strength requirements, the ceramic may have an increased tricalcium phosphate content. A Ca/P and HA/TCP ratio has been identified that balances all the requirements of a carrier for BMP in non-load bearing fusion applications, such as posterolateral fusions, or for use with a cage or metal fixation in load bearing fusions. In some cases the TCP content may approach 100%.

Even in non-load bearing applications, strength of the ceramic is an important consideration. The ceramic must be handled by the surgeon and must resist compression by overlying muscles to maintain a space for bone formation. A minimal amount of HA, preferably about 5%, is required for this purpose.

Advantageously, the spinal implants of the present invention may not require internal fixation. The implants are contained by the compressive forces of the surrounding muscles. Temporary external mobilization and support of the instrumented and adjacent vertebral levels, with a cervical collar, lumbar brace or the like, is generally recommended until adequate fusion is achieved.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal implant, comprising:
   a body having an outer wall of a height sufficient for engagement within a space between adjacent vertebrae to maintain the space, a superior bone engaging surface, an inferior bone engaging surface, a confining matrix between said surfaces for confining new bone growth to said matrix, said confining matrix having pores and including a biphasic calcium phosphate ceramic having between about 2–40% hydroxyapatite and between about 98–60% tricalcium phosphate by volume; and
   a therapeutically effective amount of a bone growth inductive factor entrapped within said matrix.

2. The spinal implant of claim 1, wherein said ceramic has a calcium/phosphorous ratio of between about 1.50 to about 1.60.

3. The spinal implant of claim 2, wherein said ceramic has a calcium/phosphorous ratio of about 1.51.

4. The spinal implant of claim 1, wherein said bone growth inductive factor is a bone morphogenetic protein.

5. The spinal implant of claim 4, wherein said bone morphogenetic protein is selected from the group consisting of BMP-1, BMP-2, BMP-3, BMP-4, BMP-5, BMP-6, BMP-7, BMP-8, BMP-9, BMP-10, BMP-11, BMP-12 and BMP-13.

6. The spinal implant of claim 5, wherein said bone morphogenetic protein is a heterodimer of at least two BMPs selected from said group.

7. The spinal implant of claim 6, wherein said heterodimer is a BMP-2 and BMP-7 heterodimer.

8. The spinal implant of claim 4, wherein said bone morphogenetic protein is a bovine extracted BMP.

9. The spinal implant of claim 1, wherein said implant has a kidney-shaped cross-section to conform to the shape of vertebral endplates.

10. The spinal implant of claim 1, wherein said body is rectangular-shaped.

11. The spinal implant of claim 1, wherein said implant has a weight ratio of bone growth inductive factor to ceramic of no more than about 1:200.

12. The spinal implant of claim 11, wherein said implant has a weight ratio of bone growth inductive factor to ceramic of between about 1:200 and about 1:2000.

13. The spinal implant of claim 12, wherein said implant has a weight ratio of bone growth inductive factor to ceramic of about 1:1250.

14. The spinal implant of claim 1, wherein said biphasic calcium phosphate ceramic has a pore size from about 200 microns to about 600 microns.

15. The spinal implant of claim 1, wherein said biphasic calcium phosphate ceramic has a porosity between about 60% to about 80%.

16. The spinal implant of claim 15, wherein said porosity of about 70%.

17. The spinal implant of claim 1, wherein said biphasic calcium phosphate ceramic includes between about 2–20% hydroxyapatite and about 80–98% tricalcium phosphate by volume.

18. The spinal implant of claim 17, wherein said biphasic calcium phosphate ceramic includes between about 5–20% hydroxyapatite and about 80–95% tricalcium phosphate.

19. The spinal implant of claim 18 wherein said biphasic calcium phosphate ceramic includes about 20% hydroxyapatite and about 80% tricalcium phosphate.

20. An osteoinductive composition comprising:
   a biphasic calcium phosphate ceramic carrier including between about 2–40% hydroxyapatite and about 98–60% tricalcium phosphate by volume; and
   a therapeutically effective amount of a bone growth inductive factor dispersed within said carrier for controlled formation of new bone within said carrier.

21. The osteoinductive composition of claim 20, wherein said ceramic carrier includes between 2–20% hydroxyapatite and between 80–98% tricalcium phosphate by volume.

22. The osteoinductive composition of claim 21, wherein said ceramic carrier includes between 5–20% hydroxyapatite and 80–95% tricalcium phosphate by volume.

23. The osteoinductive composition of claim 22, wherein said ceramic carrier includes 20% hydroxyapatite and 80% tricalcium phosphate by volume.

24. The osteoinductive composition of claim 20, wherein said ceramic carrier has a calcium/phosphorous ratio of between about 1.50 to about 1.60.

25. The osteoinductive composition of claim 24, wherein said ceramic carrier has a calcium/phosphorous ratio of about 1.51.

26. The osteoinductive composition of claim 20, wherein said bone growth inductive factor is a bone morphogenetic protein.

27. The osteoinductive composition of claim 26, wherein said bone morphogenetic protein is selected from the group consisting of BMP-1, BMP-2, BMP-3, BMP-4, BMP-5, BMP-6, BMP-7, BMP-8, BMP-9, BMP-10, BMP-11, BMP-12 and BMP-13.

28. The osteoinductive composition of claim 27, wherein said bone morphogenetic protein is a heterodimer of at least two BMPs selected from said group.

29. The osteoinductive composition of claim 26, wherein said bone morphogenetic protein is a recombinant human BMP.

30. The osteoinductive composition of claim 26, wherein said bone morphogenetic protein is a bovine extracted BMP.

31. The osteoinductive composition of claim 20, wherein said composition has a ratio of bone growth inductive factor to ceramic of no more than about 1:200.

32. The osteoinductive composition of claim 31, wherein said composition has a ratio of factor to ceramic of between about 1:200 to about 1:2000.

33. The osteoinductive composition of claim 32, wherein said composition has a ratio of factor to ceramic of about 1:1250.

34. The osteoinductive composition of claim 20, wherein said ceramic carrier is a body having a porosity between about 60% to about 80%.

35. The osteoinductive composition of claim 34, wherein said porosity is about 70%.

36. The osteoinductive composition of claim 20, wherein said ceramic carrier is a body having a pore size from about 200 microns to about 600 microns.

37. The osteoinductive composition of claim 20, wherein said ceramic carrier is in granular form.

38. A carrier for controlled delivery of a bone growth inductive factor, comprising a porous biphasic calcium phosphate ceramic having between about 2–40% hydroxyapatite and about 98–60% tricalcium phosphate, said ceramic having a calcium/phosphorous ratio of between about 1.50 to about 1.60.

39. The carrier of claim 38, wherein said ceramic has a calcium/phosphorous ratio of about 1.51.

40. The carrier of claim 38, wherein said ceramic is in the form of a body having a porosity between about 60% to about 80%.

41. The carrier of claim 40, wherein said porosity is about 70%.

42. The carrier of claim 38, wherein said ceramic has a pore size from about 200 microns to about 600 microns.

43. The carrier of claim 38, wherein said ceramic includes between about 2–20% hydroxyapatite and about 80–98% tricalcium phosphate by volume.

44. The carrier of claim 43, wherein said ceramic includes between about 5–20% hydroxyapatite and about 80–95% tricalcium phosphate by volume.

45. The carrier of claim 44, wherein said ceramic includes about 20% hydroxyapatite and about 80% tricalcium phosphate by volume.

46. An implant, comprising:
   a porous ceramic body defining a confining matrix for confining new bone growth within said body; and
   a therapeutically effective amount of a bone growth inductive factor entrapped within said matrix at a weight ratio of bone growth inductive factor to ceramic of no more than about 1:200.

47. The spinal implant of claim 46, wherein said weight ratio is between 1:200 and 1:2000.

48. The implant of claim 47, wherein said weight ratio is about 1:1250.

49. The implant of claim 46, wherein said ceramic is a biphasic calcium phosphate ceramic.

50. The implant of claim 46, wherein said bone growth inductive factor is a bone morphogenetic protein.

* * * * *

UNITED STATES PATENT AND TRADEMARK OFFICE
CERTIFICATE OF CORRECTION

PATENT NO. : 6,037,519
APPLICATION NO. : 08/955003
DATED : March 14, 2000
INVENTOR(S) : William F. McKay Page 1 of 1

It is certified that error appears in the above-identified patent and that said Letters Patent is hereby corrected as shown below:

In the claims

Column 9, line 42, now reads: "98-60%"
                should read -- 60-98% --

Column 10, line 33, now reads: "98-60%"
                should read -- 60-98% --

Column 11, line 23, now reads: "98-60%"
                should read -- 60-98% --

Signed and Sealed this

Thirteenth Day of October, 2009

David J. Kappos
*Director of the United States Patent and Trademark Office*